US009480468B2

(12) United States Patent
Tegels

(10) Patent No.: US 9,480,468 B2
(45) Date of Patent: Nov. 1, 2016

(54) DISTAL BALLOON BOND FOR TEMPORARY SEALING LOCATION DEVICE AND METHODS

(75) Inventor: Zachary J. Tegels, Minneapolis, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 160 days.

(21) Appl. No.: 14/113,255

(22) PCT Filed: Apr. 18, 2012

(86) PCT No.: PCT/US2012/034004
§ 371 (c)(1),
(2), (4) Date: Jan. 8, 2014

(87) PCT Pub. No.: WO2012/148745
PCT Pub. Date: Nov. 1, 2012

(65) Prior Publication Data
US 2014/0114349 A1 Apr. 24, 2014

Related U.S. Application Data
(60) Provisional application No. 61/478,691, filed on Apr. 25, 2011.

(51) Int. Cl.
*A61B 17/08* (2006.01)
*A61D 1/00* (2006.01)
(Continued)

(52) U.S. Cl.
CPC .... *A61B 17/0057* (2013.01); *A61B 2017/0065* (2013.01); *A61B 2017/00557* (2013.01); *A61B 2017/00659* (2013.01); *A61B 2017/00672* (2013.01); *A61B 2017/22067* (2013.01)

(58) Field of Classification Search
CPC ................ A61B 17/0057; A61B 2017/00672; A61B 2017/0065; A61B 2017/00659; A61B 2017/22067; A61B 2017/22051
See application file for complete search history.

(56) References Cited

U.S. PATENT DOCUMENTS 5,292,332 A * 3/1994 Lee ............................... 606/213
5,643,292 A 7/1997 Hart
(Continued)

FOREIGN PATENT DOCUMENTS

WO 2004093649 A2 11/2004
WO 2010027693 A2 3/2010
(Continued)

OTHER PUBLICATIONS

PCT International Search Report for PCT International Patent Application No. PCT/US2012/034004, mailed Oct. 2, 2012.

*Primary Examiner* — Melanie Tyson
(74) *Attorney, Agent, or Firm* — Holland & Hart

(57) ABSTRACT

A vascular closure system (10) includes a dual lumen tube (14), an inflatable balloon (16), and a distal sealing assembly (18). The dual lumen tube includes a proximal end portion, a distal end portion, a first lumen, and a second lumen. The first lumen is coupled in fluid communication with an inflation fluid and has a first distal opening at a distal end of the dual lumen tube. The second lumen extends from the proximal end portion to the distal end portion. The inflatable balloon is mounted to the dual lumen tube in fluid communication with the first lumen, and is inflatable within a vessel to temporarily seal closed a tissue puncture. The distal sealing assembly includes a distal sealing member (74) positioned distal of the inflatable balloon, and is detachable from the distal sealing assembly at a location exterior and adjacent to the vessel.

8 Claims, 8 Drawing Sheets

(51) Int. Cl.
*A61B 17/00* (2006.01)
*A61B 17/22* (2006.01)

(56) References Cited

U.S. PATENT DOCUMENTS

| | | | | |
|---|---|---|---|---|
| 5,868,778 | A * | 2/1999 | Gershony | A61M 25/06 604/96.01 |
| 6,059,800 | A | 5/2000 | Hart et al. | |
| 7,163,523 | B2 * | 1/2007 | Devens, Jr. | A61L 29/04 604/525 |
| 2004/0176801 | A1 | 9/2004 | Edwards et al. | |
| 2005/0228443 | A1 * | 10/2005 | Yassinzadeh | 606/213 |
| 2009/0088793 | A1 * | 4/2009 | Bagaoisan et al. | 606/213 |
| 2009/0171281 | A1 | 7/2009 | Pipenhagen et al. | |

FOREIGN PATENT DOCUMENTS

| | | |
|---|---|---|
| WO | 2011019374 A1 | 2/2011 |
| WO | 2011025543 A2 | 3/2011 |

* cited by examiner

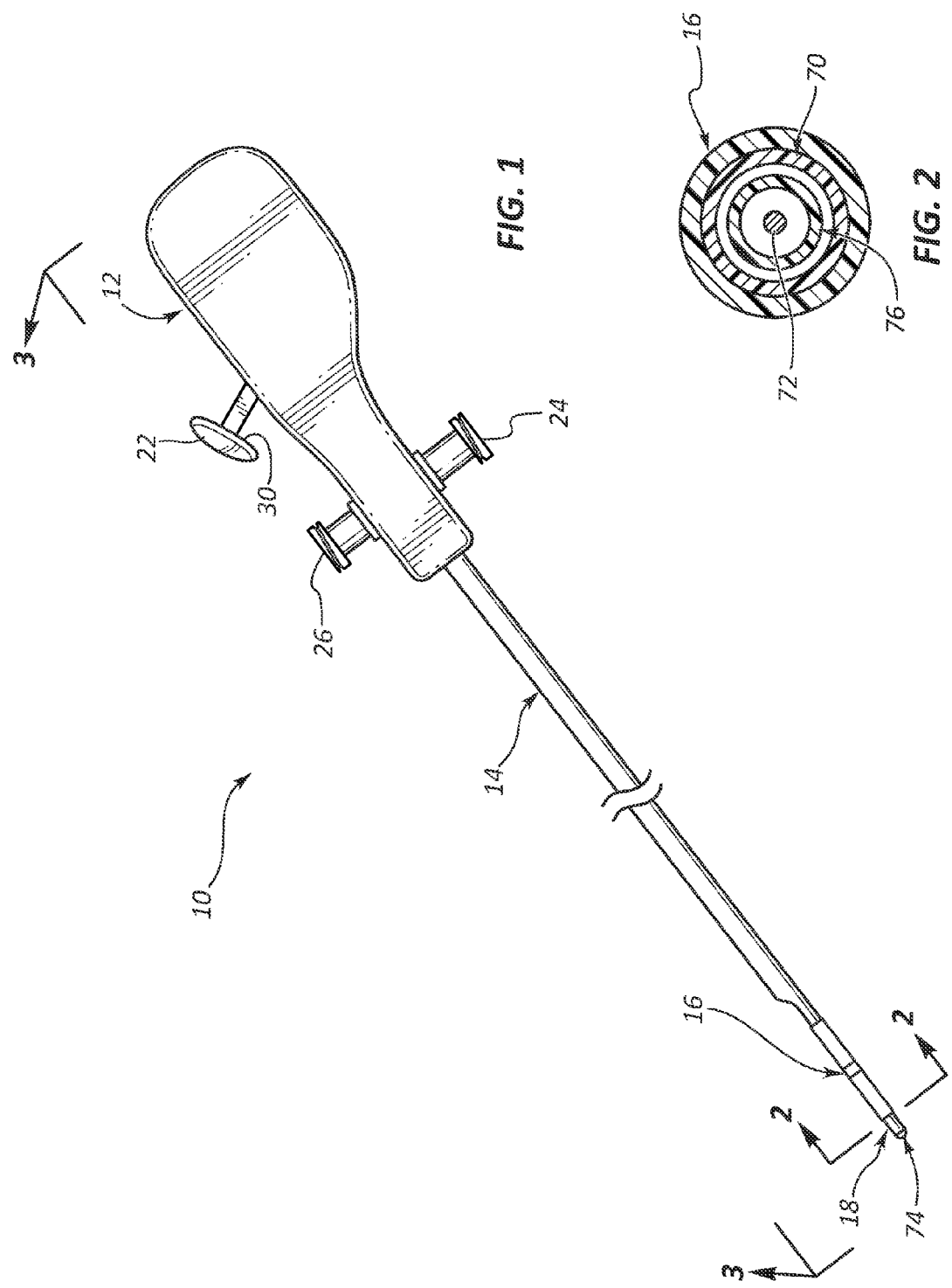

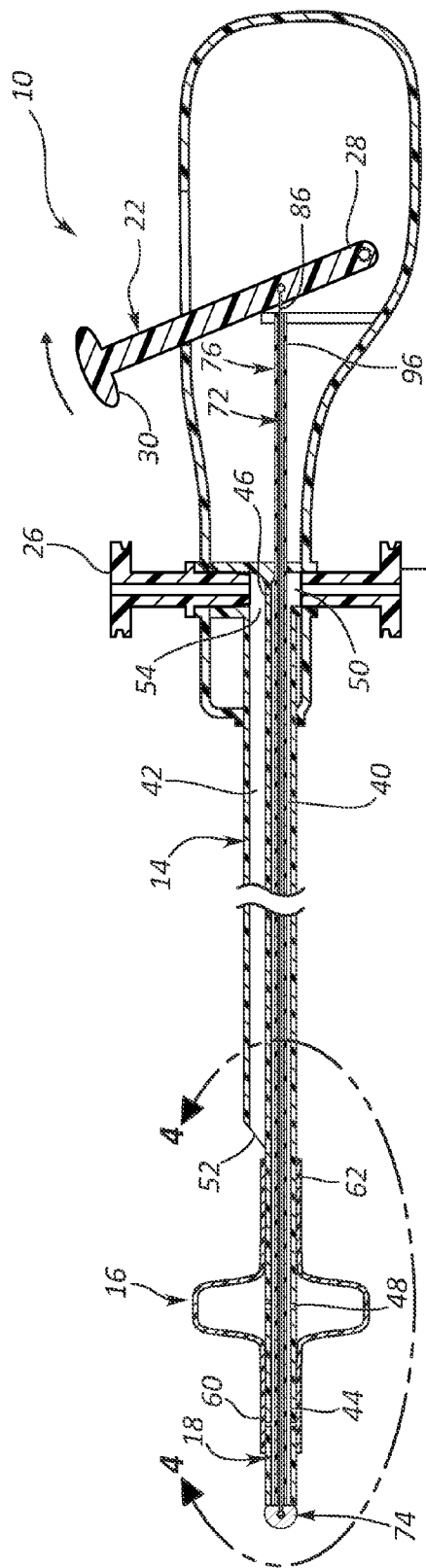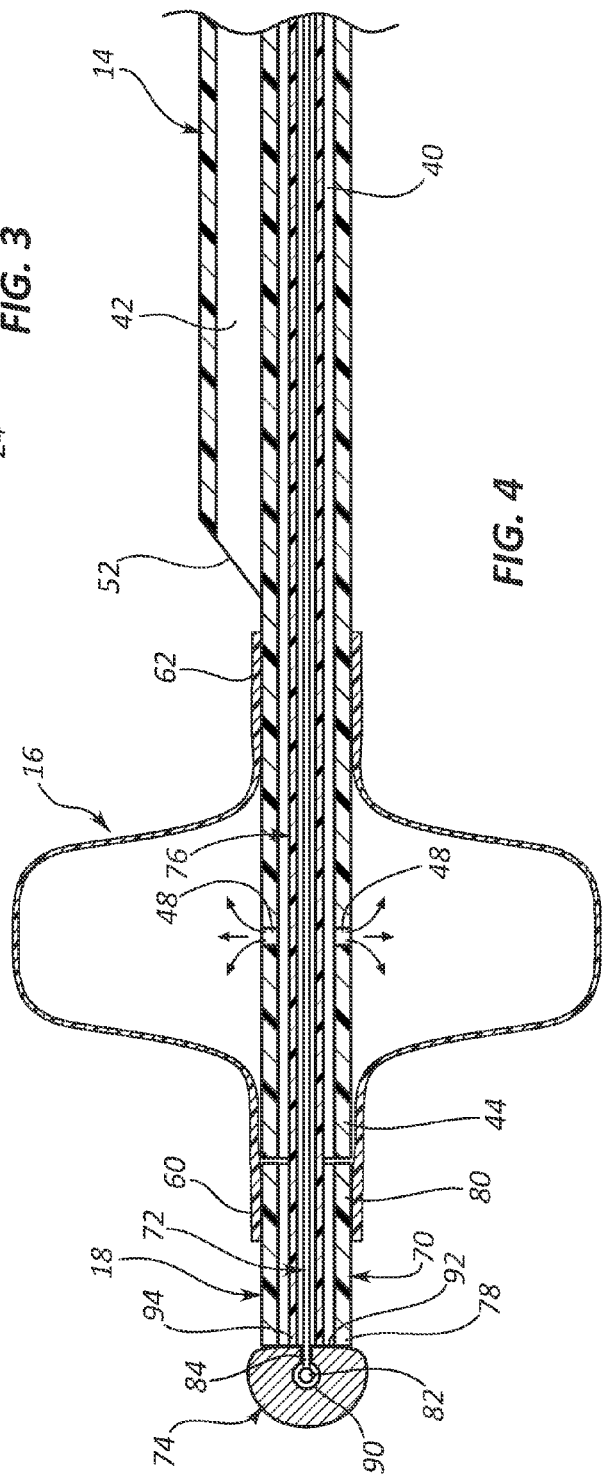
FIG. 3
FIG. 4

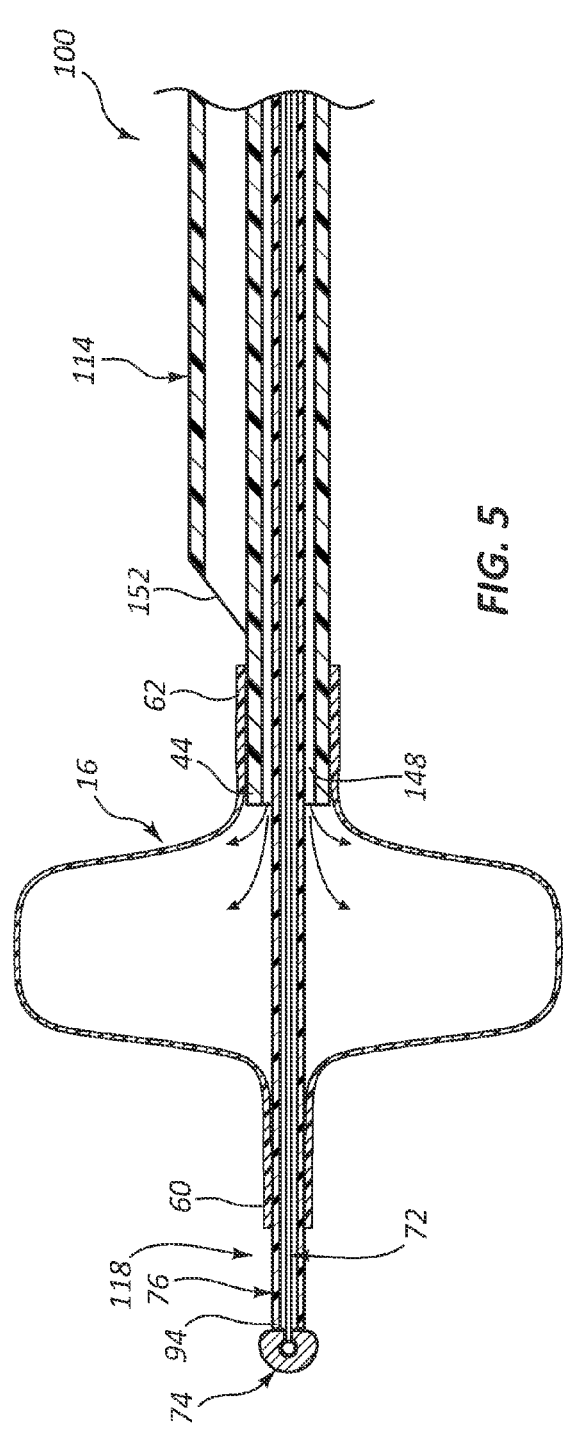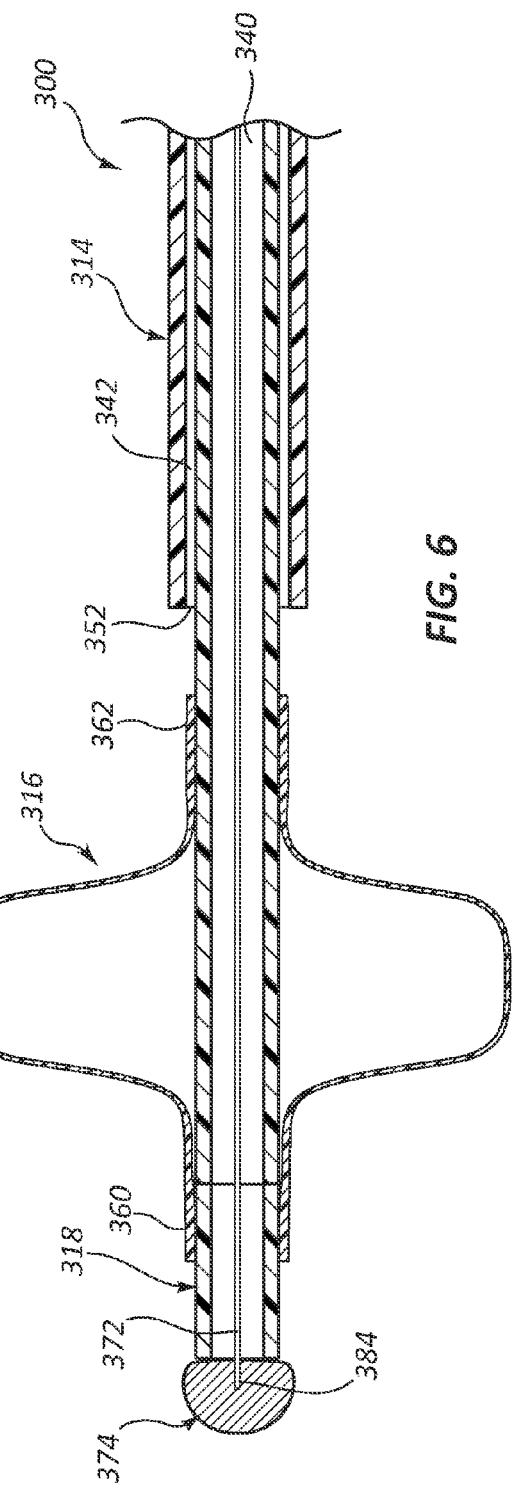

DISTAL BALLOON BOND FOR TEMPORARY SEALING LOCATION DEVICE AND METHODS

RELATED APPLICATION

This claims the benefit of U.S. Provisional Application No. 61/478,691, filed 25 Apr. 2011, which is hereby incorporated by reference herein in its entirety.

TECHNICAL FIELD

The present disclosure relates to closure devices, and more specifically relates to closure devices that place sutures across an opening in vessel wall.

BACKGROUND

Various medical procedures, particularly cardiology procedures, involve accessing a corporeal vessel through a percutaneous sheath. The sheath necessarily requires the formation of a hole or opening in the vessel wall so that a medical procedure can be performed via the sheath. After the particular medical procedure has been performed, the sheath must eventually be removed from the vessel and the access hole in the vessel wall must be closed.

A number of prior vascular closure devices have been developed in attempting to provide a solution for the problem of closing a hole in the vessel wall. Tissue approximation typically involves passing a length suture into and through adjacent vessel and subcutaneous tissue, across the vessel opening, and back into and through adjacent vessel and subcutaneous tissue. Certain prior closure devices have involved relatively complicated methods and devices for extracting a length of suture from inside the vessel so that the physician can approximate tissue surrounding the hole in the vessel wall through use of the suture.

U.S. Pat. Nos. 5,643,292 and 6,059,800 disclose example prior suturing devices used for approximating tissue surrounding the opening in a vessel wall. Most prior closure devices enlarge the vessel opening thereby negating the benefits of using smaller or less invasive percutaneous products. Prior suturing devices are also relatively complicated and difficult to use.

There remains a need, therefore, to provide a suturing apparatus that is relatively simple in construction, is easy to use, and can effectively approximate tissue surrounding an opening in a vessel wall. There is further a need to provide a suturing device that minimizes the invasiveness of the suturing procedure.

SUMMARY

One aspect of the present disclosure relates to a vascular closure system that includes a dual lumen tube, an inflatable balloon, and a distal sealing assembly. The dual lumen tube includes a proximal end portion, a distal end portion, a first lumen, and a second lumen. The first lumen is coupled in fluid communication with an inflation fluid and has a first distal opening at a distal end of the dual lumen tube. The second lumen extends from the proximal end portion to the distal end portion. The inflatable balloon is mounted to the dual lumen tube in fluid communication with the first lumen, and is inflatable within a vessel to temporarily seal closed a tissue puncture. The distal sealing assembly includes a distal sealing member positioned distal of the inflatable balloon and is detachable from the distal sealing assembly at a location exterior and adjacent to the vessel.

The second lumen may be configured as a blood flashback lumen. The second lumen may be configured as a bioadhesive ejection lumen, wherein a bioadhesive is ejected through the second lumen to the vessel. The distal sealing assembly further comprises a pull wire, and the distal sealing member is mounted to the pull wire. The vascular closure system may include a pull wire tube extending through the first lumen, and a pull wire extending through the pull wire lumen. The distal sealing member may be releasably mounted to a distal end of the pull wire. The distal sealing member may include a bioresorbable material. The second lumen defines a second distal opening spaced proximal of the first distal opening. The distal sealing assembly may include a distal balloon tube, and the inflatable balloon may be mounted at a proximal end to the dual lumen tube and mounted at a distal end to the distal balloon tube.

Another aspect of the present disclosure relates to a vascular closure device that includes an inflation balloon and a distal assembly. The inflation balloon includes a distal balloon waist and is inflatable to temporarily seal closed a vessel puncture from within a vessel. The distal assembly includes a distal tube, a wire member, and a distal sealing plug. The distal tube has a distal end and a proximal end, wherein the distal balloon waist of the inflation balloon is mounted to the distal tube. The wire member has a free distal end extending beyond the distal end of the distal tube. The distal sealing plug is mounted to the distal end of the wire member and is detachable from the wire member upon withdrawal of the vascular closure device through the vessel puncture to at least in part seal closed the vessel puncture.

A proximal end of the wire member may be fixed to the distal tube. The distal tube may terminate at the inflation balloon. A proximal end of the wire member may include at least one pre-bend feature, and the distal tube may include a sealed proximal end. The at least one pre-bend feature may be mounted to the sealed proximal end of the distal tube. The vascular closure device may also include a wire tube extending through the inflation balloon and into the distal tube, wherein the wire member extends through the wire tube.

A further aspect of the present disclosure relates to a method of closing a vascular opening in a vessel wall. The method includes providing a vascular closure device having an inflation balloon and a distal sealing member positioned distal of the inflation balloon, positioning the inflation balloon and distal sealing member through the vascular opening, and inflating the inflation balloon and contacting the inflation balloon against the vessel wall to temporarily seal closed the vascular opening. The method may also include delivering a sealing material to a vascular opening outside of the vessel wall and at least partially curing the sealing material to seal closed the vascular opening, deflating the inflation balloon, withdrawing the inflation balloon through a balloon tract in the at least partially cured sealing material, and detaching the distal sealing member within the balloon tract to seal closed the balloon tract.

The vascular closure device may include a dual lumen tube comprising an inflation lumen and a flashback lumen, and the method may include transporting inflation fluid to/from the inflation balloon through the inflation lumen, and providing flashback blood flow through the flashback lumen prior to temporarily sealing closed the vascular opening with the inflation balloon. Delivering the sealing material may include delivering the sealing material through the flashback lumen. The vascular closure device may include a wire member that connects the distal sealing member to the vascular closure device, and detaching the distal sealing member may include disconnecting the distal sealing member from the wire member.

The wire member may include a proximal end that extends proximally from the vascular closure device, and detaching the distal sealing member may include actuating the wire member. The vascular closure device may include a wire member that connects the distal sealing member to the vascular closure device, and detaching the distal sealing member may include disconnecting the wire member from the vascular closure device. Disconnecting the distal sealing member from the wire member may include actuating an actuator at a proximal end portion of the vascular closure device.

The foregoing and other features, utilities, and advantages of the invention will be apparent from the following detailed description of the invention with reference to the accompanying drawings.

BRIEF DESCRIPTION OF THE DRAWINGS

FIG. 1 is a side view of an example vascular closure system in accordance with the present disclosure.

FIG. 2 is a cross-sectional view of the vascular closure system shown in FIG. 1 taken along cross-section indicators 2-2.

FIG. 3 is a cross-sectional view of the vascular closure system of FIG. 1 taken along cross-section indicators 3-3.

FIG. 4 is a detailed view of a distal end portion of the vascular closure system shown in FIG. 3 with an inflated expandable balloon.

FIG. 5 is a cross-sectional view of a distal end portion of another example vascular closure system in accordance with the present disclosure.

FIG. 6 is a cross-sectional view of a distal end portion of another example vascular closure system in accordance with the present disclosure.

DETAILED DESCRIPTION

Figure 8:
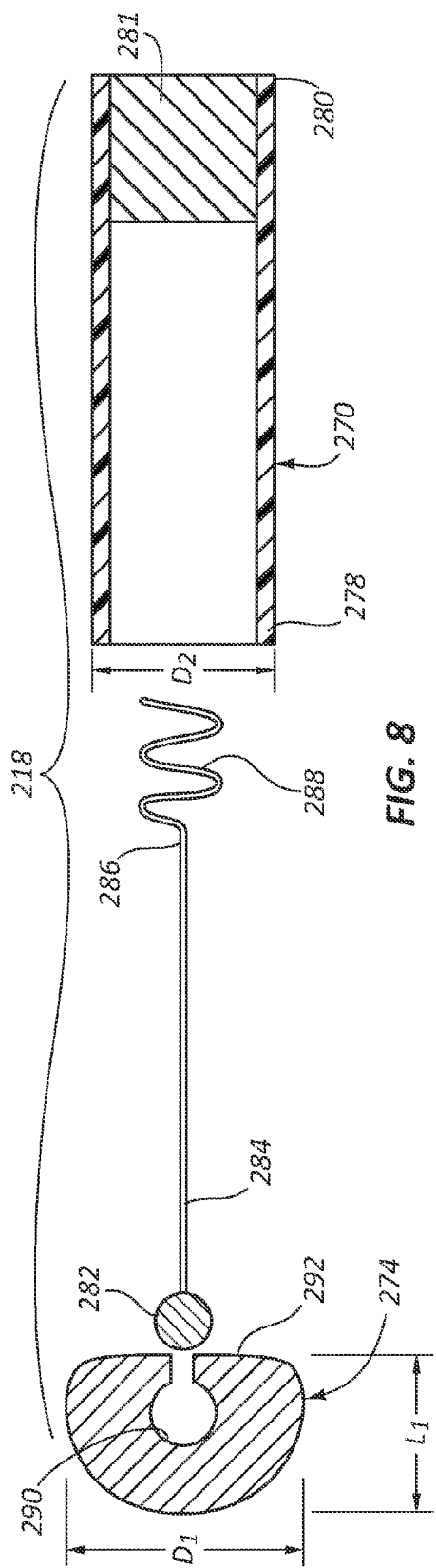
FIG. 8 is an exploded cross-sectional view of a distal sealing assembly of the vascular closure system of FIG. 7.

The present disclosure is directed to systems, devices and methods for closing an opening in a tissue layer. An example application is a vascular closure system used to close a vessel puncture. The vascular closure system may include a closure device used to temporarily seal closed the vessel puncture while delivering a sealing material to the puncture site. The sealant may be deposited on an exterior surface of the vessel adjacent to the vessel puncture to provide hemostasis upon removal of the closure device. The vascular closure system may be operable to seal closed a vessel puncture extravascularly without the use of sutures or other structure that physically closes the vessel puncture.

One aspect of the present disclosure is directed to a vascular closure system that deposits a sealing material adjacent to the vessel puncture along an outer surface of the vessel to provide a fluid seal with the vessel wall. The vascular closure system may also be configured to deposit a sealing plug within a hollow tract or cavity of the sealing material that is created when removing the vascular closure system from the vessel puncture. The sealing plug may be disengageable upon manual actuation, while in other embodiments the sealing plug may automatically disconnect from the vascular closure system and be deposited within the sealing material upon removal of the vascular closure system from the vessel puncture.

The vascular closure system may include a dual lumen tube. One lumen of the dual lumen tube may be used to deliver an inflation fluid to an inflatable member such as a expandable balloon that is positioned at a distal end of the vascular closure system. A second lumen of the dual lumen tube may operate as a flashback lumen with a distal open end positioned at a distal end portion of the vascular closure system, and a proximal opening at a proximal end portion of the vascular closure system. The second lumen of the dual lumen tube may in some arrangements operate as a delivery lumen for delivering a sealant to a location adjacent to the vascular opening. In some arrangements, the second lumen of the dual lumen tube may operate as a both a flashback lumen and a sealant delivery lumen. The lumens of the dual lumen tube may be arranged either side-by-side or coaxially. The dual lumen tube may in other embodiments include other lumen arrangements, such as three or more lumens, or a single lumen.

The vascular closure system may include a distal sealing assembly that includes a distal balloon tube, a detachable sealing member or detachable sealing plug, and other features used to provide releasable connection of the detachable sealing member to the vascular closure system. In some arrangements, the detachable sealing member is connected to the vascular closure system with a wire member. The wire member may extend to a proximal end portion of the vascular closure system where the wire member can be manipulated to detach the detachable sealing member. In other arrangements, the wire member extends along only a portion of the length of the vascular closure system (e.g., remain distal of the inflatable member of the vascular closure system) and be operable to automatically disconnect from the detachable sealing member during use of the vascular closure system. In some arrangements, the detachable sealing member is connected to the vascular closure system with a bioresorbable member such as a bioresorbable suture that is permanently connected to the detachable sealing member. Cutting the suture at any location along the length of the suture may disconnect the detachable sealing member from the vascular closure system.

Referring now to FIGS. 1-4, an example vascular closure system 10 includes a handle assembly 12, a dual lumen tube 14, an inflatable balloon 16, and a distal sealing assembly 18. The handle assembly 12 is positioned at a proximal end of the dual lumen tube 14. The inflatable balloon 16 and distal sealing assembly 18 are positioned at a distal end of the dual lumen tube 14.

A handle assembly 12 includes a housing 20, an actuator handle 22, an inflation port 24, and a flashback port 26 (also referred to as a sealant port 26 or a flashback/sealant port 26). The actuator handle 22 may extend from the housing 20 or be configured in any manner to be accessible by an operator. Referring to FIG. 3, the actuator handle 22 may include a pivot end 28 positioned within the housing 20 and an actuator end 30 accessible from outside of the housing 20. The pivot end 28 may be pivotally connected within the housing 20 to permit rotation of the actuator handle 22 between a forward or advanced position (see FIG. 3), and a rearward or retracted position (see FIG. 14). Other types of actuator configurations may be possible to provide relative movement between a wire member 72 of the distal sealing assembly 18 and the dual lumen tube 14 to disconnect to the detachable sealing member 74 from the vascular closure system 10.

The inflation port 24 is configured to connect a source of inflation fluid to the vascular closure system 10. The flashback port 26 may provide an outlet or open proximal end of a lumen of the dual lumen tube 14 that carries flashback fluid (e.g., blood) to indicate a position of a distal end portion of the vascular closure system 10 relative to a vessel interior. The flashback port 26 may also function as a sealant port or sealing material port connected in fluid communication with a supply of sealing material or sealant. A volume of sealant may be directed through sealant port 26 and along the dual lumen tube 14 to be deposited in a location adjacent to a vessel opening to help seal closed the vessel opening.

Figure 13:
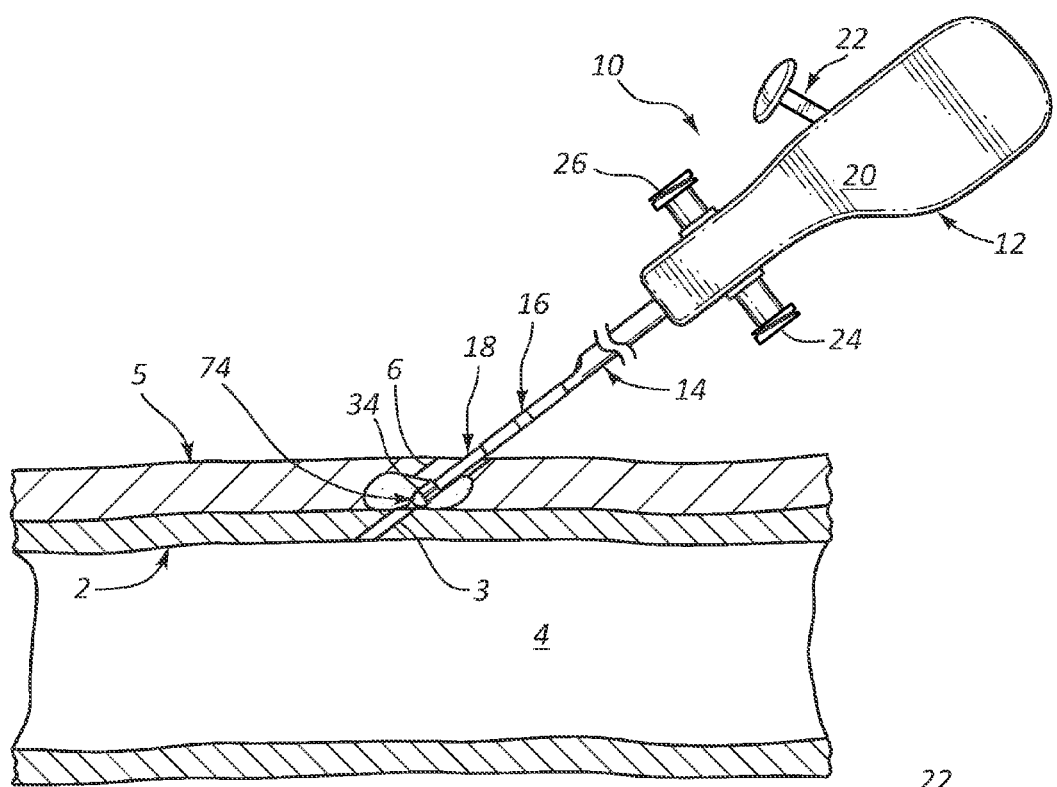

The sealant delivered to the vessel opening typically surrounds the dual lumen tube 14 and creates a fluid seal against an exterior surface of the vessel. Referring to FIG. 13, the sealant 32 is positioned adjacent to a vessel puncture or vessel opening 3 of a vessel 2. Upon removal of the vascular closure system 10, a sealant tract 34 is defined in the sealant 32. A portion of the distal sealing assembly 18 (e.g. a detachable sealing member 74) may be deposited within the sealant tract 34 to improve sealing of the vessel puncture 3 (see FIG. 14). Some types of sealant 32 may continue to flow after removal of the vascular closure system 10 to automatically constrict and seal closed the sealant tract 34. Other types of sealant may cure more quickly or cure into a structure that is less likely to automatically seal closed the sealant tract 34 without assistance from a portion of the distal sealing assembly 18. Some example sealant materials include, for example, polyethylene glycol based materials and other resorbable material that are absorbed by the body within about, for example, 30 days to 60 days.

The dual lumen tube 14 includes a first lumen 40 (also referred to as an inflation lumen 40), a second lumen 42 (also referred to as a flashback and/or sealant lumen 42), a distal end 44, and a proximal end 46. The first and second lumens 40, 42 may be arranged side-by-side or radially spaced apart (as shown in at least FIGS. 3 and 4). In other arrangements, the first and second lumens 40, 42 may be arrangement coaxially (see FIG. 6).

The inflatable balloon 16 and distal sealing assembly 18 may be positioned at the distal end 44 of the dual lumen tube 14. The proximal end 46 of the dual lumen tube 14 may be positioned within the handle assembly 12. The dual lumen tube 14 may be configured to provide fluid communication with the inflation port 24 and flashback port 26 of the handle assembly 12. FIG. 3 illustrates one example of fluid communication between the first lumen 40 and inflation port 24, and the second lumen 42 and flashback port 26.

The first lumen 40 may include distal and proximal openings 48, 50 (see FIG. 3). The second lumen 42 may include distal and proximal openings 52, 54 (see FIG. 3). The distal openings 48 may be positioned within the inflatable balloon 16 to provide fluid communication with an interior of the inflatable balloon 16. The distal opening 52 of the second lumen 42 may be positioned proximal of the inflatable balloon 16. Blood flashback through the second lumen 42 prior to inflation of the inflatable balloon 16 and after inflation of the inflatable balloon 16 and associated temporary sealing of the inflated inflatable balloon 16 against an interior surface of the vessel (see FIG. 10) may indicate to the operator whether there is blood flow through the vessel puncture 3.

The inflatable balloon 16 includes a distal balloon waist 60 and a proximal balloon waist 62. The proximal balloon waist 62 is typically mounted to an exterior surface of the dual lumen tube 14. The dual lumen tube 14 may comprise a polymer material that improves bonding to the inflatable balloon 16. In some arrangements, the dual lumen tube 14 comprises a metal material with a polymer jacket. The polymer jacket may provide a bonding surface or material to bond with the inflatable balloon 16. The inflatable balloon 16 may be bonded or connected to the dual lumen tube 14 using, for example, an adhesive, laser welding, or heat bonding. The polymer material for the dual lumen tube 14 or the polymer jacket of the dual lumen tube 14 may comprise the same or similar material as the material of the inflatable balloon 16. Some example materials include Pebax® and nylon.

The proximal balloon waist 62 is typically positioned distal of the distal opening 52 of the second lumen 42 of the dual lumen tube 14. The distal balloon waist 60 may be mounted to the distal end 44 of the dual lumen tube 14. The distal balloon waist 60 may overlap the distal end 44 of the dual lumen tube 14 and a proximal end 80 of a distal balloon tube 70 of the distal sealing assembly 18 (see FIG. 4). Alternatively, the distal balloon waist 60 may be mounted or connected directly to a wire tube 76 of the distal sealing assembly 18 or to the proximal end 80 of the distal balloon tube 70 (see FIG. 5).

The inflatable balloon 16 may expand from a contracted position shown in FIGS. 1 and 3 to an expanded position shown in FIG. 4 upon being filled with an inflation fluid. The inflation fluid may be directed through at least one distal opening 48 in the dual lumen tube 14 (see FIG. 4). In other arrangements, the inflation fluid is directed out of a distal end surface of the dual lumen tube 14 (see FIG. 5). The inflation fluid in the inflatable balloon 16 may be removed by drawing the inflation fluid back into the first lumen 40 and out through the inflation port 24.

Figure 9:
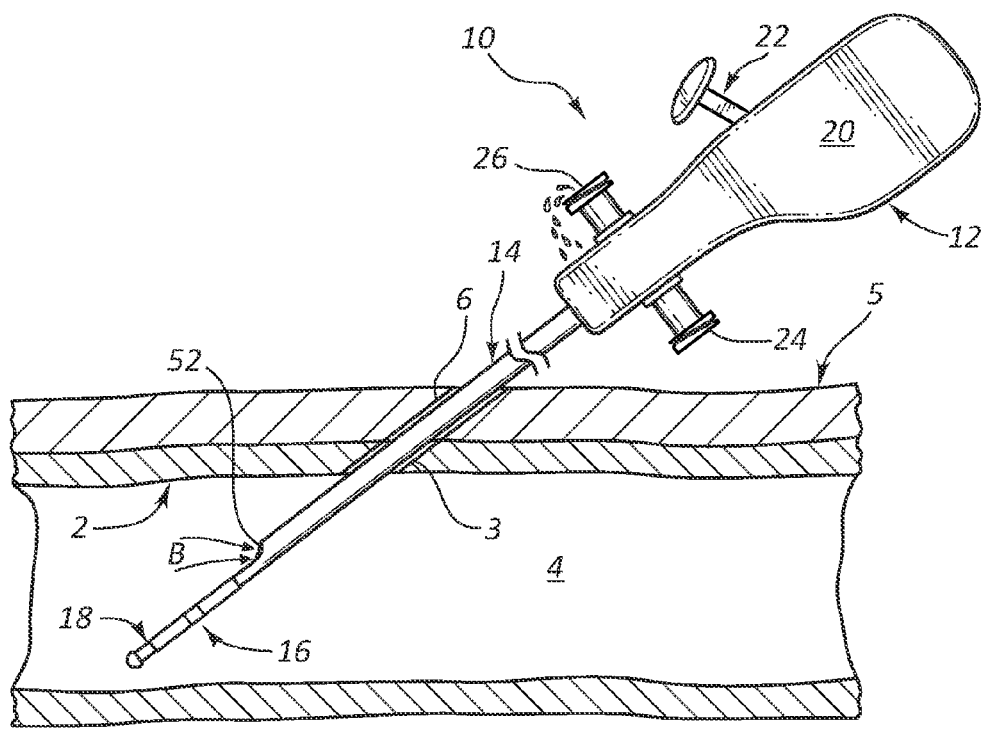
FIGS. 9-15 illustrate the vascular closure system of FIG. 1 in use sealing closed a vascular puncture in accordance with the present disclosure.

The inflatable balloon 16, when inflated, may be used to temporarily seal closed the vessel puncture 3. The nonperpendicular orientation of the vascular closure system 10 relative to the vessel 2 (see FIGS. 9 and 10) may result in some deformation of the inflatable balloon 16 when a vascular closure system 10 is retracted to contact the inflatable balloon 16 against the inner surface of the vessel 2 adjacent to the vessel puncture 3. The inflatable balloon 16 may take various shapes and have different sizes when inflated. In at least one example, the inflatable balloon 16 may change shape when drawn against an internal surface of a vessel 2 adjacent to a vessel puncture 3 as shown in, for example, FIG. 10.

The distal sealing assembly 18 includes a distal balloon tube 70, a wire member 72, a detachable sealing member 74, and a tube 76 to contain the wire 72. The distal sealing assembly 18 may be preassembled as a unit that is connected in a later assembly step to the remaining portions of the vascular closure system 10 (e.g., by bonding the distal balloon waist 60 to the distal balloon tube 70).

The distal balloon tube 70 may include distal and proximal ends 78, 80. The inflatable balloon 16 may be mounted at the proximal end 80. The detachable sealing member 74 may be positioned at the distal end 78. The distal end 78 may function as a stop surface against which the detachable sealing member 74 contacts when the wire member 72 is actuated to detach the detachable sealing member 74 from the vascular closure system 10.

The wire member 72 may include a connection member 82 at a distal end 84. A proximal end 86 of the wire member 72 extends proximately to the handle assembly 12. The proximal end 86 of the wire member 72 may be connected to the actuator handle 22 so that actuation of the actuator handle 22 moves the wire member 72 relative to at least the distal balloon tube 70.

In other arrangements, the wire member 72 may be accessible and actuatable at other locations. In one example, the wire member 72 protrudes out of a sidewall of the dual lumen tube 14 at a location distal of the proximal end 46. The proximal end 86 of the wire member 72 may be accessible for grasping by the operator to manually move the wire member 72 when disconnecting the detachable sealing member 74 from the vascular closure system 10.

The wire member 72 may have a relatively small diameter as compared to a guidewire typically used in vascular treatment procedures. In one example the wire member 72 has a diameter in the range of about 0.004 inches to about 0.01 inches, and more preferably about 0.005 inches.

The wire member 72 may be permanently connected to the vascular closure system 10. The wire member 72 may be moved longitudinally a relatively small distance to disconnect the detachable sealing member 74 from the vascular closure system 10. In one example, the wire member 72 moves less than about 1 inch, and more preferably less than 0.5 inches in order to disconnect the detachable sealing member 74 from the vascular closure system 10.

The detachable sealing member 74 may include a connection cavity 90 and a proximal surface 92. The connection cavity may be sized to receive the connection member 82 of the wire member 72. The connection member 82 may be releasably positioned within the connection cavity 90. Typically, when a threshold axial force is applied in a proximal direction to the wire member 72, the connection member 82 is releasable out of the connection cavity 90.

The proximal surface 92 of the detachable sealing member 74 typically abuts against the distal end 78 of the distal balloon tube 70. When applying the proximal directed axial force to the wire member 72, the proximal surface 92 of the detachable sealing member 74 is drawn against the proximal end 80 of the distal balloon tube 70 to act as a stop surface until the connection member 82 is pulled out of the connection cavity 90. The proximal surface 92 may also act as a catch surface that contacts the sealant when retracting the vascular closure system 10 through the sealant to help remove the detachable sealing member from the wire member 72.

The detachable sealing member 74 may comprise a bioresorbable material such as, for example, collagen, algenate, polyglycolide, co-polymer, polyethylene, glycol, L-lactide, or D-lactide. The detachable sealing member 74 may have sufficient rigidity to maintain its shape during delivery of the vascular closure system 10 through the vessel puncture 3 and into the vessel 2, and maintain that shape and size until the detachable sealing member 74 is detached within the sealant 32, as shown in at least FIG. 14. The detachable sealing member 74 may comprise a plurality of materials arranged as, for example, layers with different rigidity or other properties.

The wire tube 76 extends from the distal end 78 of the distal balloon tube 70 to the housing 20. The wire tube 76 may include distal and proximal ends 94, 96. The wire tube may comprise, for example, a stainless steel material with a polymer jacket. The polymer jacket may be useful for bonding other features of the vascular closure system 10 to the wire tube 76 (e.g., a distal balloon waist 60 of the inflatable balloon 16). Typically, the inner diameter of the wire tube 76 is greater than the outer diameter of the wire member 72. Providing the wire tube 76 with a high tensile strength material such as stainless steel may make it possible to reduce the inner diameter of the wire tube 76 relative to the outer diameter of the wire member 72 while providing a low friction contact between the wire member 72 and the wire tube 76. Other types of materials are possible for the wire tube 76 including, for example, polymer base materials.

Referring to FIG. 5, another example vascular closure system 100 includes a dual lumen tube 114 that terminates proximal of the distal balloon waist 60 of the inflatable balloon 16. The distal balloon waist 60 is connected directly to the wire tube 76.

The distal sealing assembly 118 may include a wire member 72, a detachable sealing member 74, and a wire tube 76, and be operable without a distal balloon tube 70 as described with reference to the vascular closure system 10 described above. The vascular closure system 100 may have a reduced profile at a distal end thereof due to removal of the distal balloon tube 70 and termination of the dual lumen tube 114 proximal of the distal balloon waist 60.

Referring to FIG. 6, another example of vascular closure system 300 is shown including a dual lumen tube 314, an inflatable balloon 316, and a distal sealing assembly 318. The dual lumen tube 314 includes first and second lumens 340, 342, and a distal end 344 having a distal opening 352. The first and second lumens 340, 342 are arranged coaxially with each other. The distal opening 352 is opened around a periphery of the first lumen 340. The inflatable balloon 316 is mounted to the dual lumen tube 314 with a distal balloon waist 360 and a proximal balloon waist 362 connected directly to the first lumen 340.

The distal sealing assembly 318 includes a distal balloon tube 370, a wire member 372, and a detachable sealing member 374. The wire member 372 may be constructed of a bioresorbable material such as, for example, a suture material. The wire member 372 may be permanently connected to a detachable sealing member 374 at a distal end 384. The detachable sealing member 374 may be disconnected from the vascular closure system 300 by cutting the wire member 372 at any location along a length of the wire member 372. In one example, the wire member 372 is cut at a location within a handle assembly or at some other location distal of or proximal of the inflatable balloon 316. Various cutting devices or mechanisms may be used to cut the wire member 372.

Figure 7:
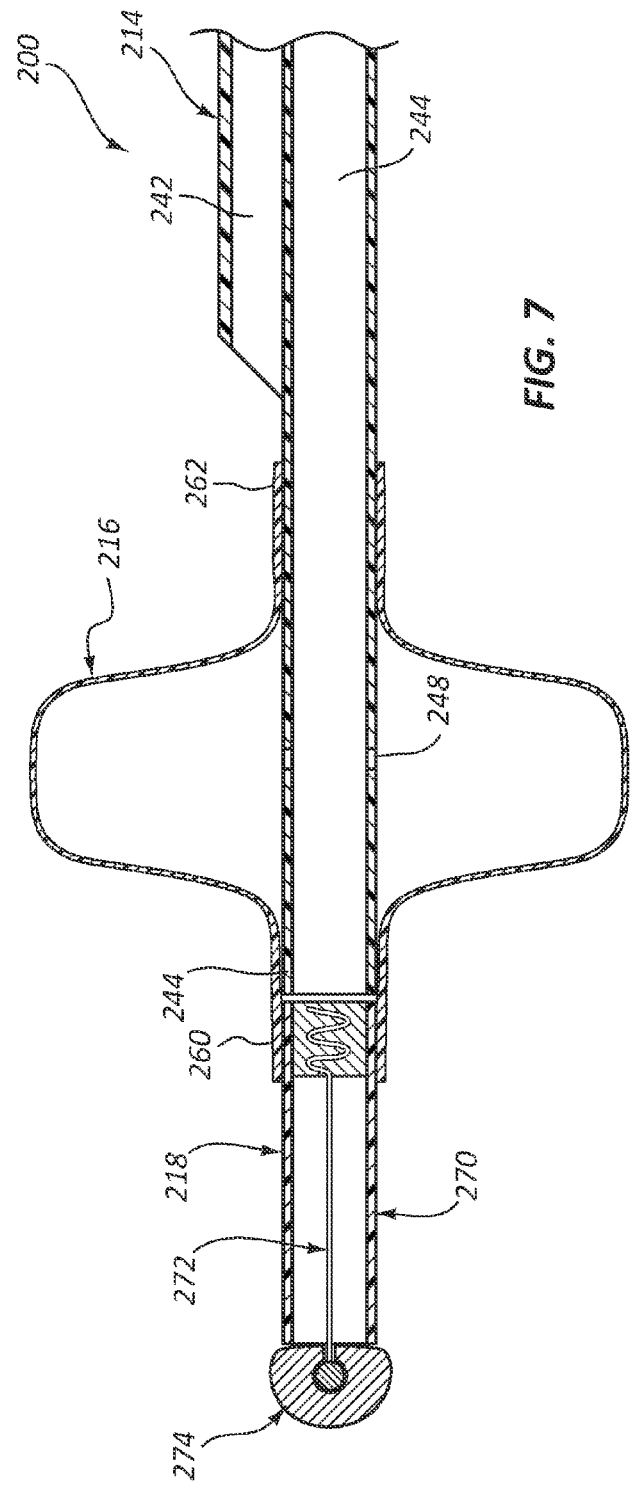
FIG. 7 is a cross-sectional view of a distal end portion of another example vascular closure system in accordance with the present disclosure.

Referring to FIGS. 7 and 8, another example vascular closure system 200 includes a dual lumen tube 214, an inflatable balloon 216, and a distal sealing assembly 218. The dual lumen tube 214 may be constructed similarly to the dual lumen tube 214 described above. The dual lumen tube 214 includes first and second lumens 240, 242 and a distal end 244. The inflatable balloon 216 includes distal and proximal balloon waists 260, 262 that are connected to the first lumen 240 at a location distal of the second lumen 242.

The distal sealing assembly 218 includes a distal balloon tube 270, a wire member 272, and a detachable sealing member 274. The distal balloon tube 270 includes distal and proximal ends 278, 280 and a plug member 281 or other support member to which the wire member 272 is mounted. The wire member 272 includes a connection member 282 at a distal end 284, and an offset proximal end 286 that includes a pre-formed bend 288. The pre-formed bend 288 may include, for example, at least one bend, coil, or other structure that is connected to the plug member 281 to retain the wire member 272 assembled with the distal balloon tube 270.

The detachable sealing member 274 includes a connection cavity 290 and a proximal surface 292. The connection member 282 is positioned within the connection cavity 290.

The detachable sealing member 274 is disconnected from the wire member 272 by applying an axial force to the detachable sealing member 274 in the distal direction by drawing the wire member 272 in the proximal direction. In at least one example, a portion of the detachable sealing member 274 such as, for example, the proximal surface 292, catches against either a portion of a vessel 2, the tissue layer 5 (see FIG. 9), or the sealant 32 (see FIG. 14) when withdrawing the vascular closure system 200 from the vessel 2. Catching a portion of the detachable sealing member 274 in this manner may apply the distally directed axial force to the detachable sealing member 274 pulls the connection member 282 out of the connection cavity 290.

The distal sealing assembly 218 may be constructed as a preassembly that may be mounted or connected to the vascular closure system 200 in a separate assembly step. In at least one example, the connection member 282 is positioned within the connection cavity 290, and the preform bend 288 of the wire member 272 is connected to the plug member 281. The plug member 281 is mounted to a distal balloon tube 270. The distal sealing assembly 218 is then connected to the inflatable balloon 216 (e.g., the distal balloon waist 260 is bonded to the distal balloon tube 270). In at least some arrangements, a maximum outer dimension $D_1$ of the detachable sealing member 274 is greater than a maximum outer dimension $D_2$ of the distal end 278 of the distal balloon tube 270. This exposes a portion of the proximal surface 292 for catching when withdrawing the vascular closure system 200 through the sealant 32 and/or a percutaneous incision 6 of the tissue layer 5 to help detach the detachable sealing member 74 from the vascular closure system 200. In one embodiment, the dimension $D_1$ is in the range of about 0.03 inches to about 0.06 inches. The dimension $D_1$ may be larger than the dimension $D_2$, such as about 10% to about 50% greater in size than dimension $D_2$. The detachable sealing member 74 may have a length $L_1$ in the range of about 0.12 mm to about 0.4 mm, and more preferably about 0.2 inches to about 0.28 inches.

Referring now to FIGS. 9-15, an example method of sealing closed a vessel puncture by operation of the vascular closure system 10 is shown and described. In a first operational step, a vascular closure system 10 is inserted through a percutaneous incision 6 of a tissue layer 5 and a vessel puncture 3 of a vessel 2 until at least the distal opening 52 of the second lumen 42, the inflatable balloon 16, and distal sealing assembly 18 are positioned within a vessel interior 4. Blood flow B travels through the distal opening 52 and through the second lumen 42 and out of the flashback port 26 to indicate to the operator that the distal opening 52 is exposed to blood flow within the vessel interior 4.

Figure 10:
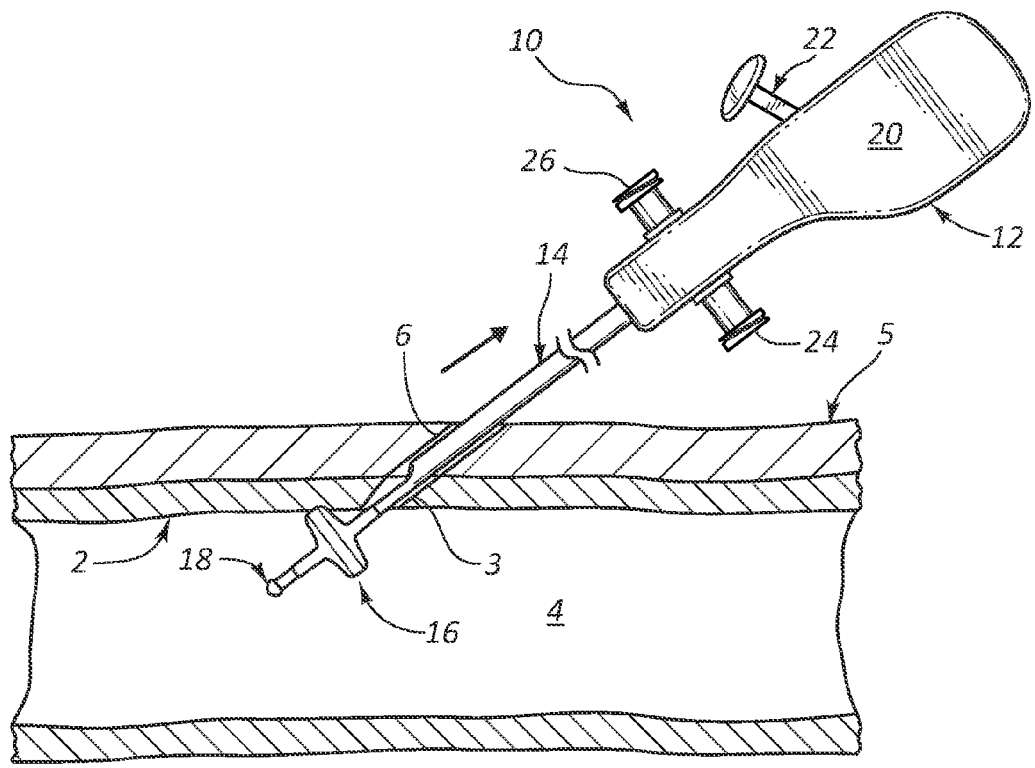

The operator may then inflate the inflatable balloon 16 to temporarily seal closed the vessel puncture 3. Typically, the inflatable balloon 16 is inflated first and the vascular closure system 10 is retracted until resistance is felt because of contact between the inflated inflatable balloon 16 and the inner surface of the vessel 2. At this point, blood flashback through the flashback port 26 should cease indicating to the operator that temporary sealing of the vessel puncture 3 is complete. FIG. 10 illustrates the inflated inflatable balloon 16 temporarily sealing closed the vessel puncture 3 and flashback blood flow having ceased through the flashback port 26.

Figure 11:
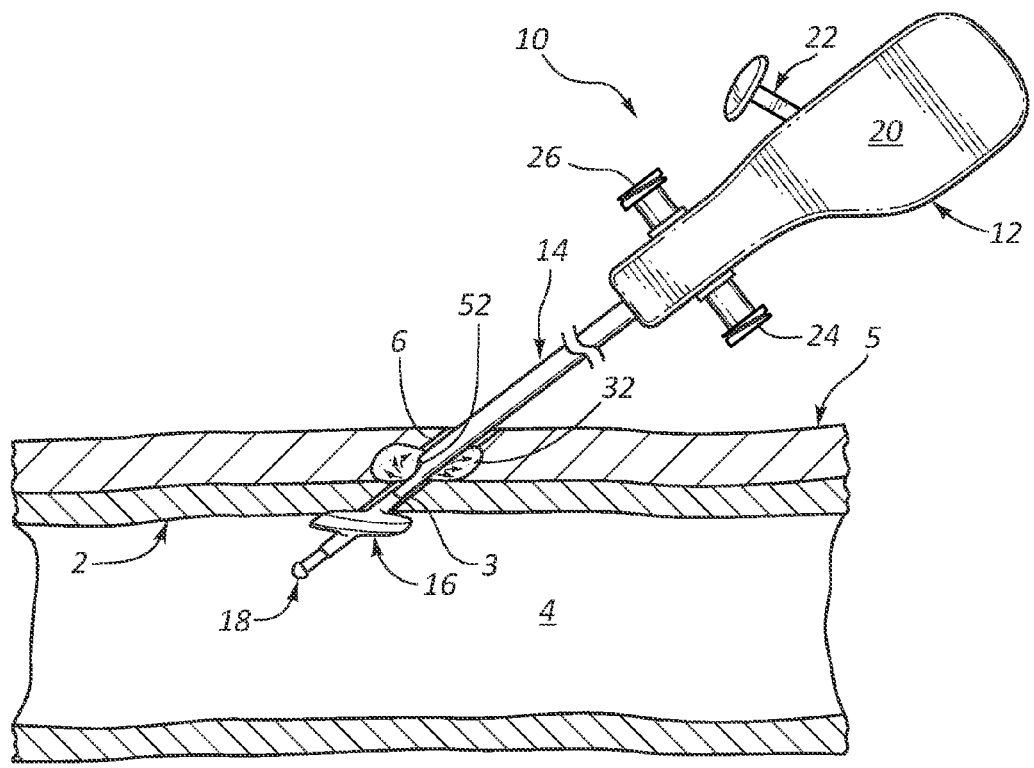

Referring now to FIG. 11, the operator may deliver a sealant 32 to a location exterior of the vessel interior 4 and adjacent to the vessel puncture 3. The sealant 32 may be delivered in any desired manner and may comprise any desired sealant material. In one example, the sealant 32 is delivered through the second lumen 42 and comprises a fluid, gel, or semi-gel material that flows around the dual lumen tube 14 and at least partially cures to create a fluid tight seal against an outer surface of the vessel 2 adjacent to the vessel puncture 3. Typically, the inflatable balloon 16 is maintained inflated during delivery of the sealant 32 to limit flow of the sealant 32 through the vessel puncture 3 and into the vessel interior 4.

Figure 12:
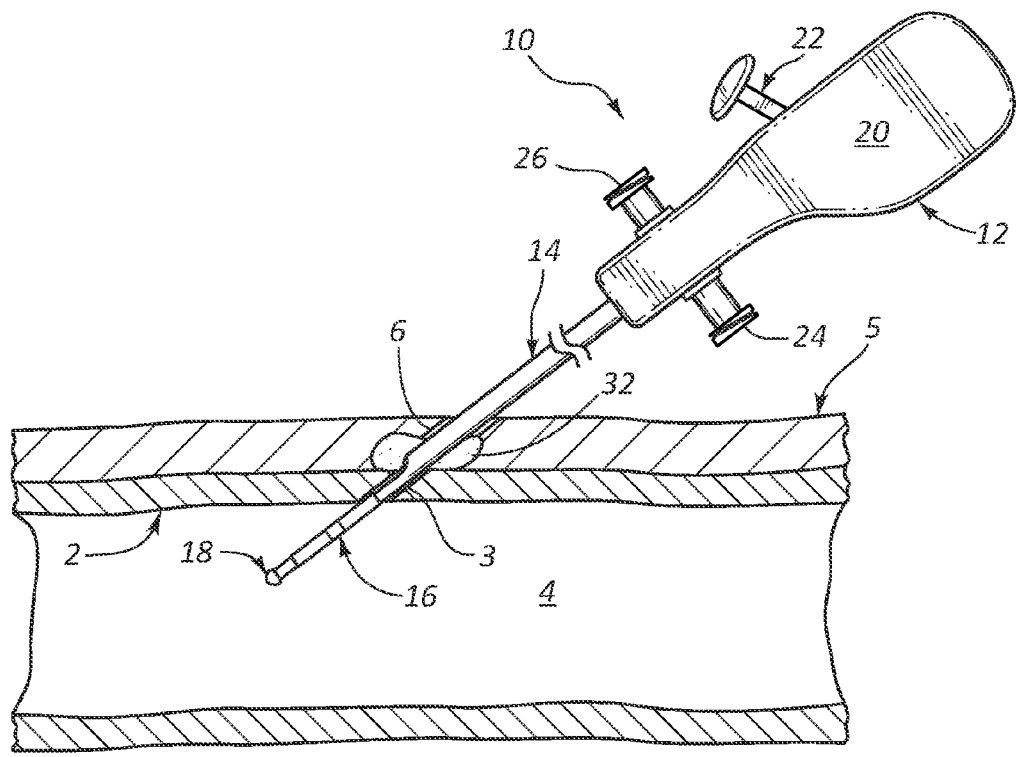

The sealant 32 is permitted to at least partially cure into a solid or semi-solid state in which it is less likely that the sealant 32 will inadvertently pass through the vessel puncture 3 into the vessel interior 4. The inflatable balloon 16 is deflated by removing inflation fluid through the inflation port 24 as shown in FIG. 12. The dual lumen tube 14 typically defines or helps form a sealant tract 34 through the sealant 32. In at least some examples, the sealant 32 continues to flow to close the sealant tract 34 upon removal of the vascular closure system 10 from the vessel 2 and through the sealant 32. In other examples, the sealant tract 34 remains at least partially open thereby permitting at least some blood flow there through upon removal of the vascular closure system 10.

Referring to FIG. 13, the operator positions the detachable sealing member 74 out of the vessel 2 and preferably within the sealant 32. In some arrangements, the detachable sealing member 74 may be positioned directly adjacent to an exterior of the vessel puncture 3. In still further arrangements, the detachable sealing member 74 is positioned within the vessel puncture 3 and outside of the vessel interior 4.

Figure 14:
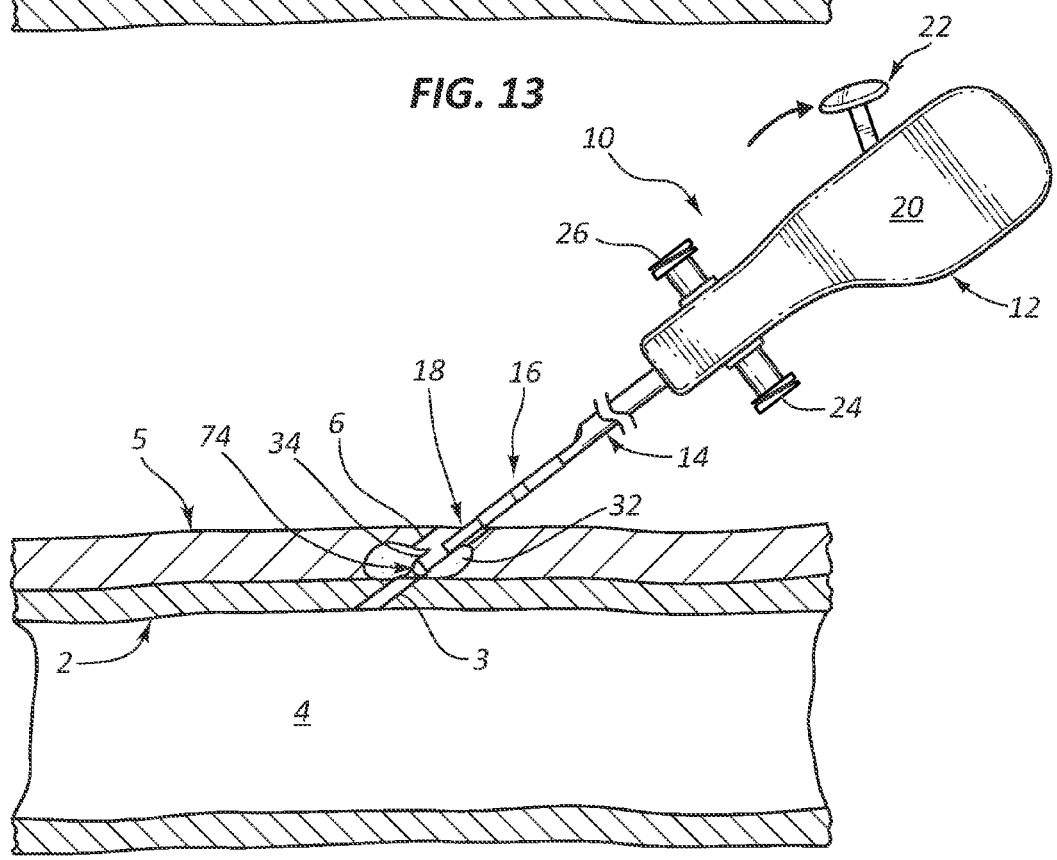
Figure 15:
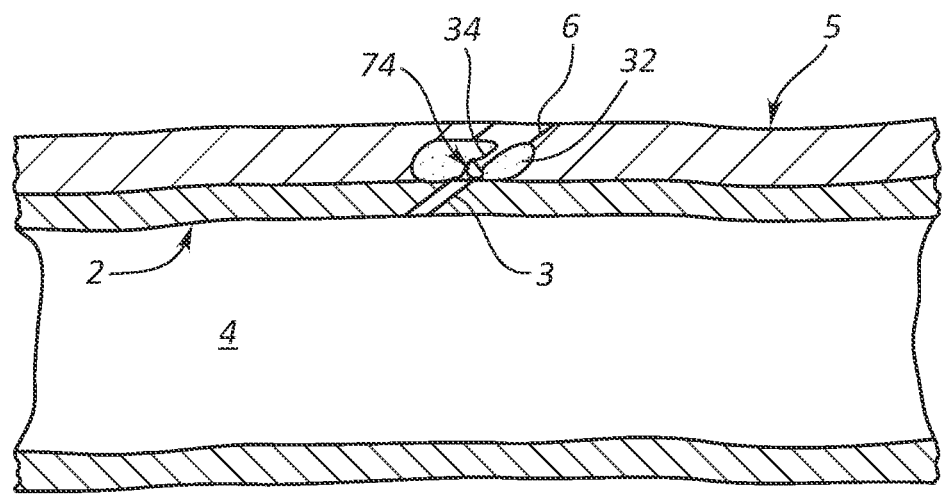

Referring to FIG. 14, the operator actuates the actuator handle 22 to move the wire member 72 and detach the detachable sealing member 74 from the vascular closure system 10. The detachable sealing member 74 remains lodged within the sealant 32 to seal closed the sealant tract 34 as shown in FIG. 15. The vessel puncture 3 is sealed closed without the use of sutures or other devices besides the sealant 32 and detachable sealing member 74.

The example vascular closure systems described herein include an inflatable balloon. Other arrangements are possible in which the inflatable balloon is replaced with other anchor features such as, for example, an expandable mechanical anchor or other type of anchoring device.

The example vascular closure systems described with reference to the figures each include a dual lumen tube. Other arrangements are possible in which the tube used to support the distal sealing assembly into which the handle assembly is mounted includes a single lumen. Some arrangements may include multiple tubes whether arranged coaxially, side-by-side, or along only a portion of the length of each other.

Furthermore, many distal sealing assemblies are possible that provide manual or automatic detachment of a detachable sealing member when withdrawing the vascular closure system from a vessel puncture. In other arrangements, the distal sealing assembly may include other features or functionality besides the use of a detachable sealing member to assist in sealing closed the vessel puncture extravascularly.

While this invention has been described with reference to certain specific embodiments and examples, it will be recognized by those skilled in the art that many variations are possible without departing from the scope and spirit of this invention. The invention, as defined by the claims, is intended to cover all changes and modifications of the invention which do not depart from the spirit of the invention. The words "including" and "having," as used in the specification, including the claims, shall have the same meaning as the word "comprising."

What is claimed is:

1. A vascular closure system, comprising:
   a dual lumen tube having a proximal end portion and a distal end portion, the dual lumen tube comprising:
   a first lumen coupled in fluid communication with an inflation fluid and having a first distal opening at a distal end of the dual lumen tube;
   a second lumen extending from a proximal end portion of the distal end portion of the dual lumen tube, the second lumen being connected to the first lumen and to a sealant delivery port, the second lumen having a distal opening that opens in a distal direction;
   an inflatable balloon mounted to the dual lumen tube in fluid communication with the first lumen, the inflatable balloon being inflatable within a vessel to temporarily seal closed a tissue puncture;
   a distal sealing assembly comprising a distal sealing member positioned distal of the inflatable balloon, the inflatable balloon being in contact with the distal sealing assembly, the distal sealing member being detachable from the distal sealing assembly at a location exterior and adjacent to the vessel.

2. A vascular closure system according to claim 1 wherein the second lumen is configured as a blood flashback lumen.

3. A vascular closure system according to claim 2 wherein the second lumen is configured as a bioadhesive ejection lumen, a bioadhesive being ejectable through the second lumen to the vessel.

4. A vascular closure system according to claim 1 wherein the distal sealing assembly further comprises a pull wire, the distal sealing member being mounted to the pull wire.

5. A vascular closure system according to claim 1 further comprising a pull wire tube extending through the first lumen, and a pull wire extending through the pull wire lumen, the distal sealing member being releasably mounted to a distal end of the pull wire.

6. A vascular closure system according to claim 1 wherein the distal sealing member includes a bioresorbable material.

7. A vascular closure system according to claim 1 wherein the second lumen defines a second distal opening spaced proximal of the first distal opening.

8. A vascular closure system according to claim 1 wherein the distal sealing assembly includes a distal balloon tube, the inflatable balloon being mounted at a proximal end to the dual lumen tube and being mounted at a distal end to the distal balloon tube.

* * * * *